United States Patent [19]

Hattori

[11] Patent Number: 4,527,552

[45] Date of Patent: Jul. 9, 1985

[54] ENDOSCOPE APPARATUS

[75] Inventor: Shinichiro Hattori, Tokyo, Japan

[73] Assignee: Olympus Optical Co., Ltd., Tokyo, Japan

[21] Appl. No.: 611,395

[22] Filed: May 18, 1984

Related U.S. Application Data

[63] Continuation of Ser. No. 358,183, Mar. 15, 1982, abandoned.

[30] Foreign Application Priority Data

Mar. 25, 1981 [JP] Japan .................. 56-43709

[51] Int. Cl.³ .............................. A61B 1/06
[52] U.S. Cl. ........................... 128/6; 354/62
[58] Field of Search ..................... 128/4–8; 354/62

[56] References Cited

U.S. PATENT DOCUMENTS

| 3,638,543 | 2/1972 | Kondo | 95/10 CE |
| 3,774,072 | 11/1973 | Ogawa | 315/151 |
| 4,310,228 | 1/1982 | Terada | 128/6 |
| 4,325,618 | 4/1982 | Hosoda | 128/6 |
| 4,349,014 | 9/1982 | Takamatsu | 128/6 |
| 4,349,255 | 9/1982 | Takayama | 354/62 |
| 4,367,024 | 1/1983 | Takayama | 354/62 |

Primary Examiner—Edward M. Coven
Assistant Examiner—Max F. Hindenburg

[57] ABSTRACT

In a camera attached to the eyepiece section of an endoscope is arranged a photoelectric element for generating photoelectric signal corresponding to the brightness of light reflected from an object and transmitted through an image guide in the endoscope. The photoelectric signal of the photoelectric element is converted by a current-voltage converter/integrator circuit to an observation light control signal at the time of observation while to photographing light control signal at the time of photographing. The current-voltage converter/integrator circuit also generates sync signal in response to the release action. Each of the observation light control signal, sync signal and photographing light control signal is transmitted to a light supply unit through a signal transmission line. The signal transmitted is judged through the light supply unit to be observation light control signal, sync signal or photographing light control signal according to its polarity and level. The light control of an observation light source or photographing light source is achieved according to signal judged.

8 Claims, 3 Drawing Figures

ENDOSCOPE APPARATUS

This application is a continuation, of application Ser. No. 358,183, filed Mar. 15, 1982, abandoned July 11, 1984.

BACKGROUND OF THE INVENTION

The present invention relates to an endoscope apparatus and, more particularly, an endoscope apparatus having automatic observation light control and automatic exposure functions.

An endoscope apparatus is generally designed to have observation and photographing functions and has been further provided with automatic light control and automatic exposure functions these days so as to enable observation and photographing under optimum light and right exposure. In the case of conventional endoscope apparatus, however, the photoelectric element for receiving light reflected from an object is arranged in the endoscope while the exposure calculator circuit in the light supply unit, and a long signal line is employed to connect the photoelectric element to the exposure calculator circuit. When output signal of the photoelectric element passes through the long signal line, therefore, noises are mixed with this output signal. This causes a correctly-calculated value not to be obtained and the accuracy of automatic exposure to be lowered when the exposure calculator circuit calculates exposure on the basis of the output signal of the photoelectric element. Early-opened Japanese Patent Application Sho-55/121879 discloses an endoscope apparatus in which the exposure calculator circuit is arranged in the endoscope camera so as to solve the drawback. In the case of this endoscope apparatus, however, the output signal of the photoelectric element is not transmitted to the light supply unit, thus making it impossible to automatically control observation light.

SUMMARY OF THE INVENTION

The object of the present invention is therefore to provide an endoscope apparatus capable of effecting automatic exposure and observation light control with high accuracy.

According to the present invention, a camera arranged at the eyepiece of an endoscope includes a photoelectric element and means for converting the output signal of the photoelectric element to an observation light control signal at the time of observation and to a photographing light control signal at the time of photographing. A light supply unit to which the connector of the endoscope is connected includes a circuit for discriminating the observation light control signal from photographing light control signal to light-control an observation light supply source correspondingly to the observation light control signal and a photographing light supply source correspondingly to the photographing light control signal.

DETAILED DESCRIPTION OF THE PREFERRED EMBODIMENT

Figure 1:
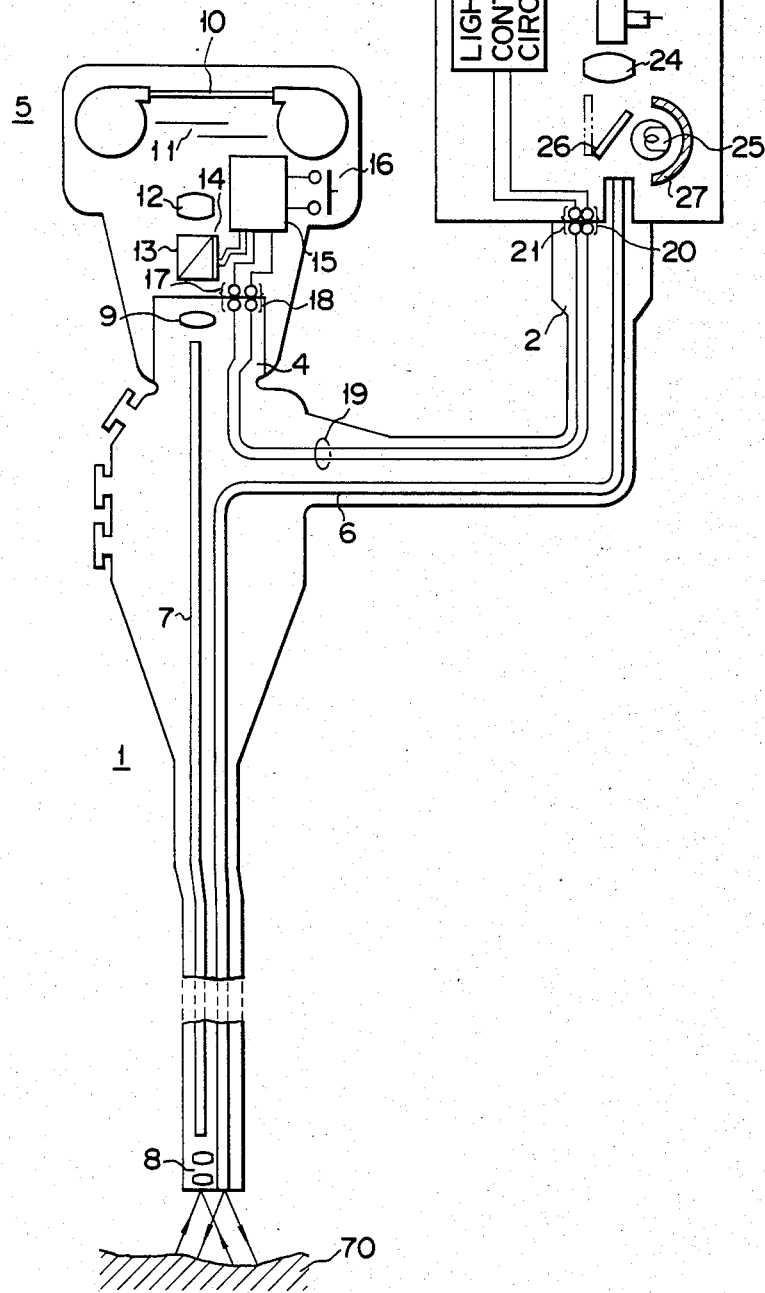
FIG. 1 schematically shows an endoscope apparatus according to an embodiment of the present invention.

Referring to FIG. 1, a light supply source connector 2 of an endoscope 1 is connected to a light supply unit 3 and an endoscope camera 5 is arranged at an endoscope eyepiece section 4. Light and image guides 6 and 7 are arranged in the endoscope 1 with the one end of image guide 7 opposite to an objective lens system 8 and the other end thereof to an ocular lens 9. A film cassette in which a film 10 is housed is arranged in the endoscope camera 5 with the film 10 opposite to a photographing lens 12 between which a shutter 11 is interposed. A beam splitter 13 is arranged between the photographing lens 12 and endoscope eyepiece section 4 in the camera 5. A photoelectric element 14 is arranged on one side of the beam splitter 13. The output terminal of the photoelectric element 14 is connected to a camera control circuit 15, to which is connected a sync switch 16. The output terminal of the camera control circuit 15 is connected through terminals 17 and 18 to a signal transmission line 19, which is connected through terminals 20 and 21 to a light supply source control circuit 22 in the light supply unit 3. A photographing light source or electronic flash tube 23 is arranged opposite to a light path changeover mirror 26 with a focusing lens 24 interposed therebetween, and an observation light supply source i.e. halogen lamp 25 having a light focusing mirror 27 is also arranged opposite to the light path changeover mirror 26 in the light supply unit 3.

Figure 2:
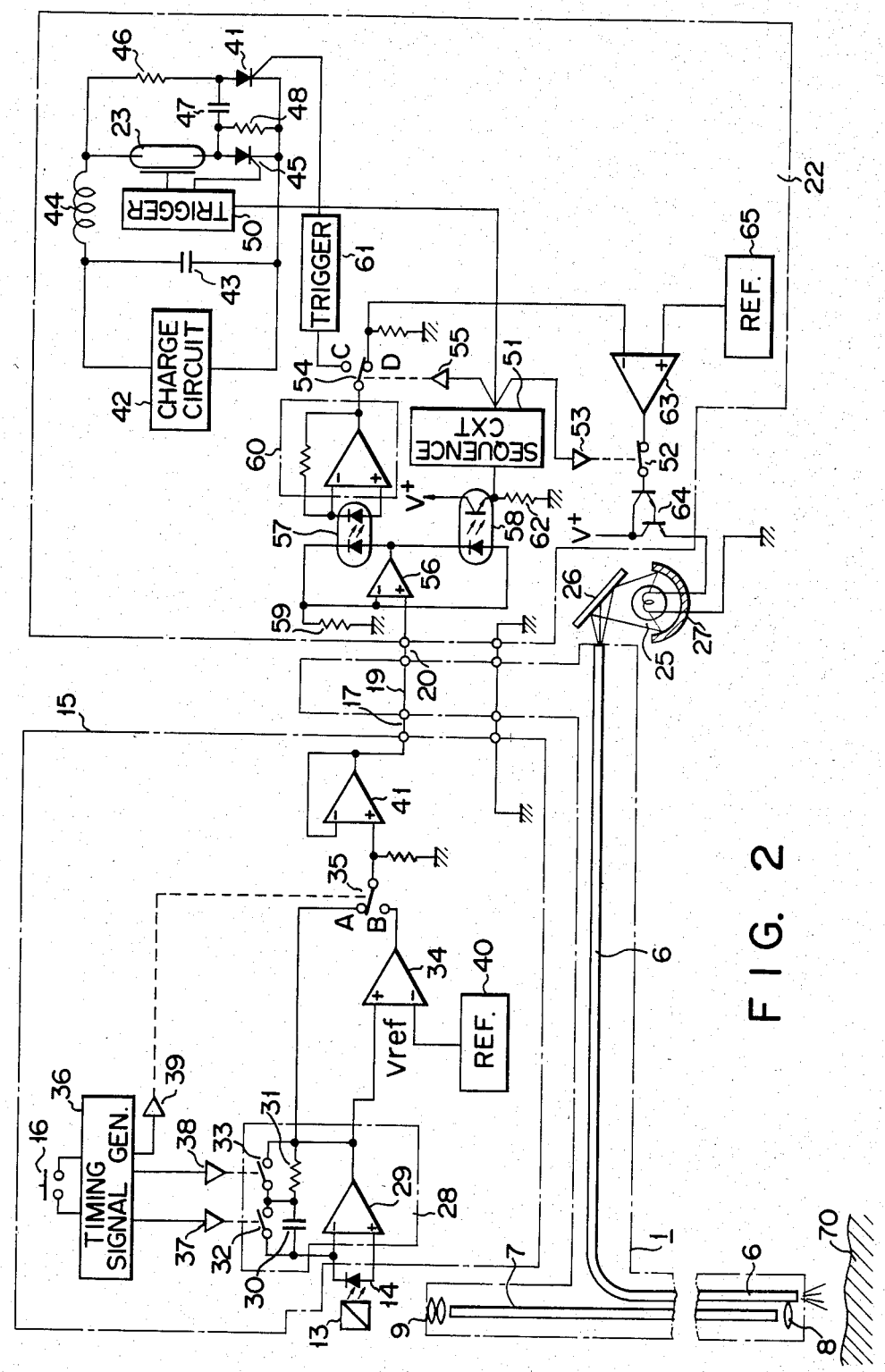
FIG. 2 shows a circuit employed in the endoscope apparatus shown in FIG. 1.

FIG. 2 shows an electric circuit for use in the endoscope apparatus described above. A current-voltage converter/integrator circuit 28 is arranged in the camera control circuit 15. The photoelectric element 14 is connected between inverted and non-inverted input terminals of an FET operational amplifier 29, and a series circuit of a capacitor 30 and a resistor 31 is connected between inverted the input terminal and output terminal of the amplifier 29 in the circuit 28. Analog switches 32 and 33 are connected to the capacitor 30 and resistor 31, respectively. The output terminal of the current-voltage converter/integrator circuit 28 is connected to the non-inverted input terminal of an operational amplifier 34, which serves as comparator, while to the contact A of an analog switch 35. The output terminal of the operational amplifier 34 is connected to the terminal B of the analog switch 35. A reference power source 40 is connected to the inverted input terminal of the operational amplifier 34. The common terminal of the analog switch 35 is connected to the non-inverted input terminal of an operational amplifier 41 which serves as a voltage follower. The output terminal of the operational amplifier 41 is connected through the terminal 17, signal transmission line 19 and terminal 20 to the non-inverted input terminal of an operational amplifier 56 in a driver circuit. The output terminal of the operational amplifier 56 is connected through the LED of a photo-coupler 57 to the inverted input terminal thereof, and this inverted input terminal is connected through the LED of a photo-coupler 58 to the output terminal thereof while earthed through a resistor 59. The photo-diode of the photo-coupler 57 is connected to a current-voltage converter 60, whose output terminal is connected to the common terminal of an analog switch 54. The terminal C of the analog switch 54 is connected to a quenching trigger circuit 61 and the terminal D thereof to the inverted input terminal of an operational amplifier 63 which serves as light quantity control amplifier. The non-inverted input terminal of the operational amplifier 63 is connected to a light quantity setting circuit 65 and the output terminal thereof to the base of a Darlington transistor through an analog switch 52. The observation lamp 25 is connected via this Darlington transistor 64 to a power supply source V+. The collector of photo-transistor of photo-coupler 58 in the driver circuit is connected to another power supply source V+ and the emitter thereof is earthed through a resistor 62 while connected to the input terminal of a sequence circuit 51, a first output terminal of which is connected to a driver 53 for the analog switch 52, a second output terminal thereof to a driver 55 for the analog switch 54, and a third output terminal thereof to a trigger circuit 50 for the electronic flash device. The output terminal of the trigger circuit 50 is connected to the trigger electrode of the electronic flash tube 23 and to the gate of a main thyristor 45 connected in series with the electronic flash tube 23. A charger circuit 42 for the electronic flash device is connected to a main capacitor 43 while via a coil 44 to a series circuit of the electronic flash tube 23 and main thyristor 45, to which a resistor 48 is connected parallel and whose anode is connected to the cathode thereof through quenching capacitor 47 and thyristor 41. The junction point between the quenching capacitor 47 and thyristor 41 is connected through a resistor 46 and the coil 44 to the charger circuit 42. The gate of the quenching thyristor 41 is connected to the output terminal of the quenching trigger circuit 61.

Figure 3:
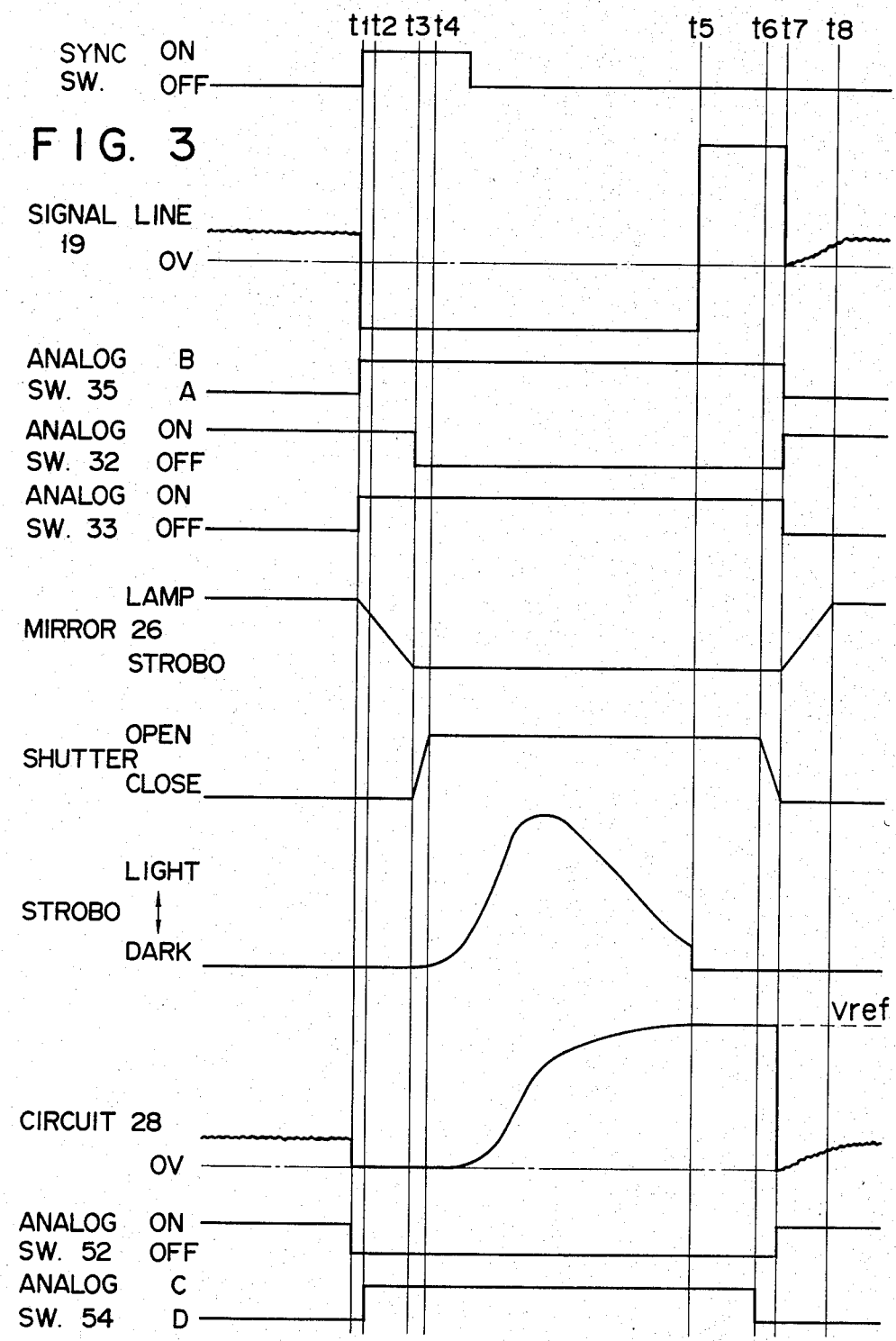
FIG. 3 is a time chart used to explain the operation of circuit shown in FIG. 2.

The operation of the endoscope apparatus having such arrangement as described will be described referring to the time chart shown in FIG. 3.

Let us explain the case of observation. The light path changeover mirror 26 in the light supply unit 3 is set as shown by a solid line so as to guide light of the observation lamp 25 into the light guide 6 in the endoscope 1. The observation light guided through the light guide 6 illuminates an object 70. Light reflected from the object 70 comes incident upon the beam splitter 13 in the endoscope camera 5 through the objective system 8, image guide 7 and ocular lens 9. A part of light incident upon the beam splitter 13 is received by the photoelectric element 14, which generates output signal corresponding to the reflected light quantity from the object 70 and supplies this output signal to the current-voltage converter/integrator circuit 28 in the camera control circuit 15. The timing signal generator circuit 36 supplies a timing signal to the drivers 37 and 38 so as to turn on analog switches 32 and 33 while to the driver 39 so as to connect the analog switch 35 to the terminal A at this time. The circuit 28 functions as current-voltage converter under this state to convert the output signal of the photoelectric element 14 to a voltage signal. This voltage signal is supplied to the voltage follower 41 through the terminal A of the analog switch 35.

The output signal of the voltage follower 41 is supplied through the terminal 17, signal transmission line 19 and terminal 20 to the non-inverted input terminal of the operational amplifier 56 included in the driver circuit in the light source control unit 22. The operational amplifier 56 operates as a kind of current signal source at this time to flow current to the resistor 59 in such a way that the same voltage as that of voltage signal supplied to the non-inverted input terminal thereof appears at the inverted input terminal thereof. Since the voltage signal at the non-inverted input terminal of the operational amplifier 56 is of positive polarity, the output terminal thereof becomes high in level to turn on the LED of the photocoupler 57. The current flowing through the LED of the photo-coupler 57 is completely proportional to signal inputted to the non-inverted input terminal of the operational amplifier 56. In addition, the current of the LED of the photo-coupler 57 is proportional to the current of the photo-diode with substantially high accuracy and the output of the current-voltage converter circuit 60 is therefore substantially proportional to the current of the LED of the photo-coupler 57 i.e. signal at the non-inverted input terminal of the operational amplifier 56 in the driver circuit. The output of the current-voltage converter circuit 60 is supplied through the terminal D of the analog switch 54 to the inverted input terminal of the operational amplifier 63, which differentially amplifies the setting signal of the light quantity setting circuit 65 and the output signal of the current-voltage converter circuit 60. The output signal of the operational amplifier 63 controls the Darlington transistor 64 through the analog switch 52 to control the light quantity of observation lamp 27. The brightness of the object 70 observed through the eyepiece section 4 is held certain thanks to this observation light quantity control. The automatic observation light control can be thus achieved in such a way that the brightness of the object 70 is held certain even if the distance between the foremost end of the endoscope 1 and the object changes.

Let us now explain the case of photographing. The release button of the endoscope camera 5, for example, is pushed in this case to effect release operation. When the sync switch 16 is turned on at a time t1 shown in FIG. 3 in response to this release operation, the analog switches 32 and 33 are turned on in response to the timing signal of the timing signal generator circuit 36, and the analog switch 35 is also connected to the terminal B. As the result, the output of the current-voltage converter/integrator circuit 28 becomes zero substantially and the operational amplifier 34 therefore outputs negative saturation voltage, which is inputted through the terminal B of the analog switch 35 to the voltage follower 41. The output or negative saturation voltage of the voltage follower 41 is supplied through the terminal 17, signal transmission line 19 and terminal 20 to the non-inverted input terminal of the operational amplifier 56 in the driver circuit. Therefore, the output of the operational amplifier 56 becomes negative in level to turn on the LED of the photo-coupler 58. The LED of the photo-coupler 57 is not lighted at this time. The photo-transistor is turned on due to the lighting of the LED of the photo-coupler 58 and a voltage appears at the resistor 62. This voltage is applied to the sequence circuit 51 to render the sequence circuit 51 operative. The sequence circuit 51 causes the driver 53 to be operated at the time t1 to turn off the analog switch 52, whereby the observation lamp 25 is turned off. A driving signal is supplied at this time t1 to a mirror driving solenoid (not shown) which moves the light path changeover mirror 26. The sequence circuit 51 renders the driver 55 operative at a time t2 to connect the analog switch 54 to the terminal C. A time difference is provided between the time t1 at which the analog switch 52 is turned off and the time t2 at which the analog switch 54 is switched over, and this is intended to prevent large current from flowing to the observation lamp 25 as a result that the non-inverted input terminal of the light control operational amplifier 63 becomes zero in level while output thereof becomes excessive. The light path changeover mirror moves to a position shown by dot-and-dash line in FIG. 1 at a time t3 and the shutter 11 begins to open. The analog switch 32 of the current-voltage converter/integrator circuit 28 in the endoscope camera 5 is also turned off at this time, whereby the circuit 28 operates as integrator circuit to start to integrate output signal of the photoelectric element 14. When the shutter 11 is fully opened at a time t4, the sequence circuit 51 inputs a light flashing signal to the trigger circuit 50. In response to this light flashing signal, the trigger circuit 50 supplies trigger signal to the trigger electrode of the electronic flash tube 23 and the gate of the main thyristor 45 to cause the electronic flash tube 23 to flash light. Light or photographing light flashed by the electronic flash tube 23 is focused by the focusing lens 24 into the light guide 6 in the endoscope 1 and illuminates the object 70 through the light guide 6. Similarly to the observation light, light reflected from the object 70 is converted to a photoelectric signal by the photoelectric element 14 in the camera 5. The output signal of this photoelectric element 14 is integrated by the circuit 28 which is now effecting integrating operation. When integrated output reaches the reference voltage Vref of the reference power source 40, the output of the operational amplifier 34 is inverted and transmitted to the signal transmission line 19 through the terminal B of the analog switch 35 and the voltage follower 41. This signal is shown at a time t5 in FIG. 3. Since the non-inverted input terminal of the operational amplifier 56 included in the driver circuit in the light source control unit 22 becomes a high positive level, the LED of the photo-coupler 57 is lighted and a high positive level signal is outputted from the current-voltage converter circuit 60. When this signal is supplied through the terminal C of the analog switch 54 to the quenching trigger circuit 61, this quenching trigger circuit 61 supplies a trigger signal to the gate of the quenching thyristor 41 to turn on this thyristor 41. As the result, the main thyristor 45 is reversely biased and turned off by voltage charged in the quenching capacitor 47 to stop the light emission of the electronic flash tube 23 and to control photographing light. The shutter 11 starts to close at a time t6 thereafter and the analog switch 54 is connected to the terminal C. The analog switch 52 is held off and the observation lamp 25 is not lighted at this time. The sequence circuit 51 causes the analog switch 52 to be switched on through the driver 53 to turn on the observation lamp 25 at a time t7 at which the shutter 11 is fully closed. The sequence circuit 51 deenergizes the light path changeover mirror driving solenoid (not shown) at this time t7 to start to return the light path changeover mirror 26 to a position shown by solid line in FIG. 1. When the light path changeover mirror 26 returns to the original position at a time t8, observation light of the observation lamp 25 is guided by the light guide 6 causing the endoscope apparatus to be held under observation state.

According to the present invention as described above, the photoelectric element output corresponding to the light quantity of the object is transmitted as observation light control signal to the signal transmitting line at the time of observation, while sync signal generated in response to the release operation and photographing light control signal for measuring the light quantity of the object and controlling photographing light are transmitted to the signal transmitting line at the time of photographing. Observation light control signal, sync signal and photographing light control signal transmitted through the signal transmitting line are applied to predetermined electrical circuit lines, respectively, to perform observation light control, flashing of the photographing light and termination of the photographing light. When thus arranged, accurate automatic exposure and automatic observation light control can be achieved without being influenced by noises. In addition, photoelectric signal, sync signal and photographing light termination signal can be transmitted from the endoscope camera to the light supply unit using a smaller number of connection pins and signal transmission lines, so that the endoscope eyepiece section and connector can be small-sized. Further, the flexible endoscope tube can be made slender to enhance the handling capability of the endoscope.

The output of the current-voltage converter circuit 60 is used to automatically control observation light at the time of observation (or at the not-photographing time) in the above-described embodiment, but this may be operationally processed with voltage charged in the main capacitor 43 or one-under or one-over exposure correcting value to judge whether automatic exposure is possible or not. An alarm means such as buzzer is arranged in the light supply unit in this case to inform the impossibility of the automatic exposure so as to prevent a right exposure photograph from being taken. Using the matter that integrated output of current-voltage converter/integrator circuit is smaller enough than that of comparator, outputs of current-voltage converter/integrator circuit and comparator may be mixed through a resistor and inputted to the voltage follower. The analog switch 35 can be omitted in this case. A current-voltage converter and an integrator may be arranged independently without using the current-voltage converter/integrator circuit and they may be switched over by an analog switch. Although flash light is electronically controlled in the above-described embodiment, the photographing light control system in which light of a lamp light source used is interrupted by a light source shutter may be employed. The circuit section including photo-couplers and the like is not necessarily arranged in the light supply unit but may be arranged in the endoscope.

What is claimed is:

1. An endoscope apparatus for performing an observation mode, and in response to a release action of a camera, for performing a photographing mode comprising:

an endoscope having an eyepiece section, a light guide for guiding observation and photographing lights towards an object, an image guide for guiding light reflected from said object to said eyepiece section, and a signal transmission line;

a camera mounted on said eyepiece section and provided with a camera circuit including photoelectric means to produce a photoelectric signal corresponding to the brightness of light reflected from the object and transmitted through the image guide to said eyepiece section;

signal generator means for converting the photoelectric signal of said photoelectric means to an observation light control signal in the observation mode and for producing a sync signal in response to a release action of said camera and for converting the photoelectric signal to a photographing light control signal in the photographing mode;

signal transmitting means for supplying said signals to the signal transmission line in the endoscope; and a light supply unit including an observation light source means for irradiating the observation light, a photographing light source means for irradiating the photographing light, and a signal discriminator circuit means connected to the signal transmission line in the endoscope to discriminate the observation light control signal, the sync signal and the photographing light control signal from one another and produce signals corresponding to these signals, respectively; said light supply unit further comprising an observation light control circuit means for controlling the light of said observation light source in response to the discriminating signal corresponding to the observation light control signal, a photographing light control circuit means for causing said photographing light source means to irradiate light in response to the discriminating signal corresponding to the sync signal and for terminating the the light emission of said photographing light source means in response to the discriminating signal corresponding to the photographing light control signal; and wherein said signal generator means comprises circuit means connected to said photoelectric means to perform the functions of (a) converting the photoelectric signal to an analog voltage signal to be used as as an observation light control signal, and (b) producing a sync signal in response to the release action, said generator means further comprising an integrator to provide the function of (c) integrating the photoelectric signal to generate an integrated signal, means for selectively switching said circuit means to perform the desired function, and means for comparing the integrated signal with a reference signal to generate digitally the photographing light control signal.

2. An endoscope apparatus according to claim 1 wherein said circuit means comprises an operational amplifier connected to the photoelectric means, a series circuit connected between the output and input terminals of said operational amplifier and composed of a capacitor and a resistor, and switching means connected parallel to the capacitor and resistor, respectively, and said means for selectively switching over includes switch control means for opening and closing the switching means.

3. An endoscope apparatus according to claim 1 wherein said signal discriminator circuit in the light supply unit includes means for discriminating said observation light control signal, sync signal, and photographing light control signal from one another using at least one of their polarities and levels.

4. An endoscope apparatus according to claim 1 or 3 wherein said discriminator circuit comprises an operational amplifier connected to the signal transmission line to generate an output signal corresponding to the polarity and level of said signal transmitted through said signal transmission line, and means connected to the output terminal of said operational amplifier to generate one of an observation indicating signal, sync indicating signal and photographing indicating signal according to this output signal of said operational amplifier.

5. An endoscope apparatus according to claim 4 wherein said indicating signal generator means comprises photo-couplers connected to the output terminal of said operational amplifier and rendered operative, respectively, in response to the polarity and level of said output signal applied from said operational amplifier.

6. An endoscope apparatus according to claim 1, 2, 3 or 5 wherein said observation light control circuit comprises a circuit for supplying to said observation light source current corresponding to the observation indicating signal.

7. An endoscope apparatus according to claim 6 wherein said observation light source is a halogen lamp.

8. An endoscope apparatus according to claim 1, 2, 3, 5 or 7 wherein said photographing light source is an electronic flash tube, and said photographing light control circuit comprises a trigger circuit for causing said electronic flash tube to be flashed in response to the sync indicating signal, and a quenching circuit for terminating the light emission of said electronic flash tube in response to the photographing indicating signal.

* * * * *